Figure 1:
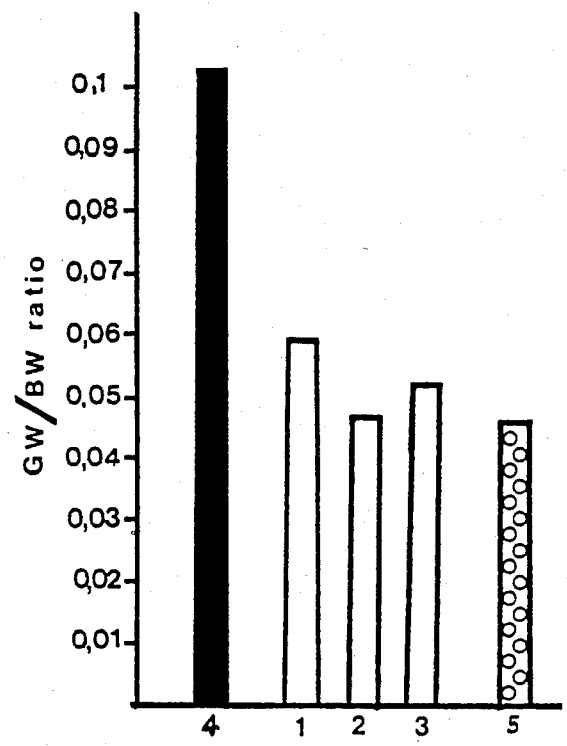

United States Patent [19]

Duflot et al.

[11] Patent Number: 4,499,080

[45] Date of Patent: Feb. 12, 1985

[54] SYNTHETIC ST TOXIN, PROCESS FOR ITS PREPARATION AND ITS USE AS A VACCINATING AGENT

[75] Inventors: Anabela Duflot, Vanves; Hélène Gras, Hem; André Tartar, Vitry-en-Artois; Edith Duflot, Cachan; Patrice Boquet, Creteil, all of France

[73] Assignee: Institut Pasteur, Paris, France

[21] Appl. No.: 488,712

[22] Filed: Apr. 26, 1983

[30] Foreign Application Priority Data

Apr. 26, 1982 [FR] France .................................. 82 07179

[51] Int. Cl.³ ...................... A61K 37/00; C07C 103/52
[52] U.S. Cl. ................................ 514/12; 260/112.5 R; 514/13; 514/14; 514/15; 514/16; 514/17; 514/18
[58] Field of Search .................. 260/112.5 R; 424/177

[56] References Cited

PUBLICATIONS

Journal of Bacteriology, (1976), p. 463–472 vol. 128, No. 1.

Primary Examiner—Delbert R. Phillips
Attorney, Agent, or Firm—Weiser & Stapler

[57] ABSTRACT

The invention relates to novel synthetic peptides, process for their peparation and their application to the production of antibodies.

These peptides include at the most 18 amino-acids and at the least 4 amino-acids in which n is equal to 1 or 2, and when n equals 1 the peptidic sequence P is contained in the following peptidic chain:

Asn-Thr-Phe-Tyr-Cys-Cys-Glu-Leu-Cys-Cys-A-Pro-Ala-Cys-Ala-Gly-Cys-T in which either A represents Asn and T represents Tyr, or A represents Tyr and T represents Asn and in which the thiol groups of the possible cysteyl residues are protected by groups stable under biological conditions. Use for the production of antibodies capable of replacing biological activity particularly of enterotoxins produced by *Escherichia coli* strains.

34 Claims, 5 Drawing Figures

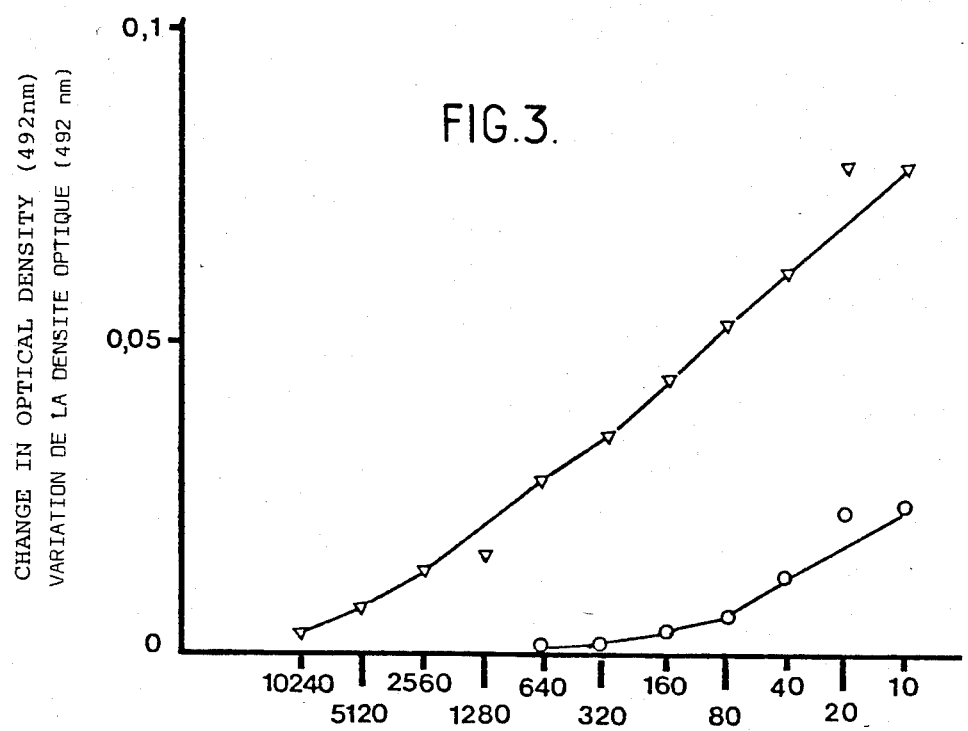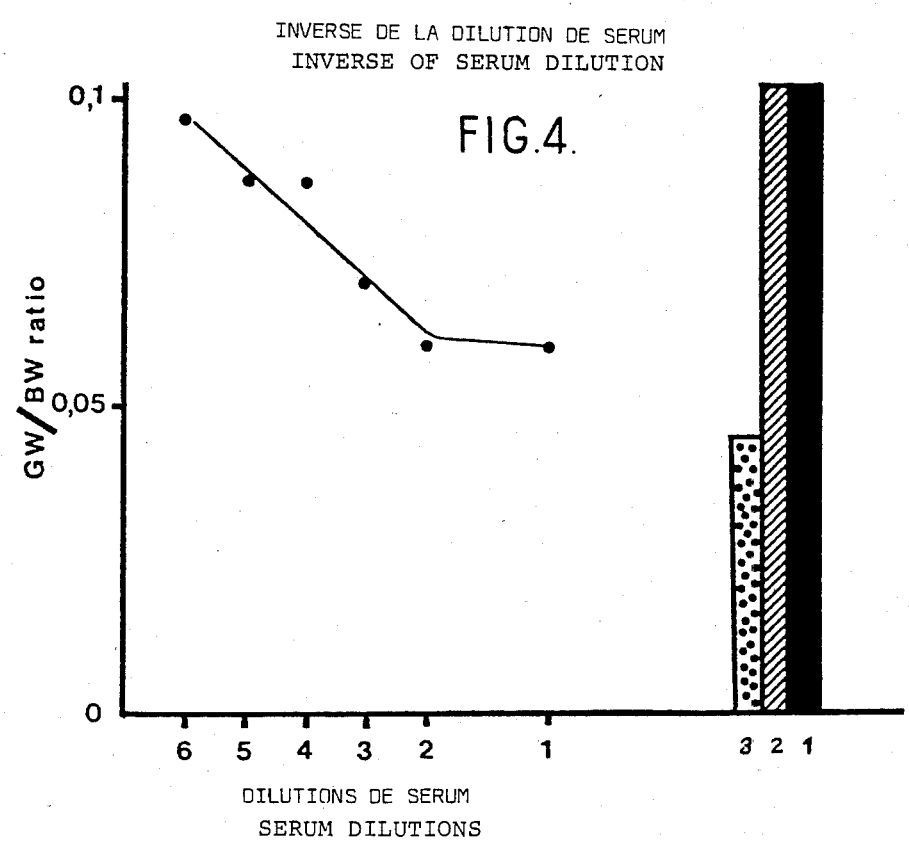

SYNTHETIC ST TOXIN, PROCESS FOR ITS PREPARATION AND ITS USE AS A VACCINATING AGENT

The invention relates to novel synthetic peptides, their process of preparation and their use for the production of antibodies capable of neutralising the biological activity of heat-stable enterotoxins, produced by *Escherichia coli* strains.

It is known that *E. coli* strains produce peptidic enterotoxins responsible for diarrhea in man and animal. At least two classes of peptidic enterotoxins have been identified of which one class is constituted by low molecular weight and heat stable enterotoxins, denoted below by "ST enterotoxins" or "natural ST enterotoxins". It is known that ST enterotoxins are encountered in multiple molecular forms which differ in molecular size, composition of amino-acids, configuration, intermolecular linkages, etc.

The multiplicity of forms in which the enterotoxins are capable of appearing, have made their identification diffcult, this all the more so as it is necessary to work with purified enterotoxins.

The purification processes known hitherto have enabled the sequence of amino-acids of an ST enterotoxin derived from pork *E. coli* to be determined (SO M. and Mc Carthy B. (1980) Proc. Natl. Acad. Sci. USA 77, 4 011–4 015) as well as the primary structure of an ST enterotoxin which derives from human *E. coli* (Chan S. K. and Gianella R. A. (1981) J. Biol. Chem. 256, 7 744–7 746).

It has thus been possible to establish that the peptidic sequence of human ST enterotoxins comprised 18 amino-acids, that the biological activity and toxicity are due to the presence of disulfide bridges and that the peptidic sequence of pig enterotoxins only differed from that of man by two amino-acids (Staples S. J., Asher S. E., and Gianella R. A. (1980) The Journal of Biological Chemistry, 225, no 10, 4 716–4 721) and (Chan S. K. and Gianella R. A. (1981), The Journal of Biological Chemistry, 256, no 15, 7 744–7 746).

It has also been shown that the first four amino-acids of human and pig ST enterotoxins were not necessary for the biological activity, whilst the last fourteen amino-acids of the sequence are biologically active and responsible for the toxicity (Chan S. K. and Giannella R. A. (1981), The Journal of Biological Chemistry, 256, no 15, 7 744–7 746).

This purification process has however the drawback of being long and complex and enables only very small amounts of purified enterotoxins to be obtained.

The difficulty of obtaining purified ST enterotoxins explains the reason why the antigenic nature of the ST enterotoxin remained poorly understood until now. It has long been thought that ST enterotoxin was not immunogenic. Contrary to this hypothesis, recent work has enabled it to be shown that ST enterotoxin, in which the disulfide bridges are present, is capable of inducing antibodies which fix the ST enterotoxin and thereby neutralise biological activity (Frantz J. C. and Robertson D. C. (1981) Infect. and Immunity, 33, 193–198), but these same antibodies are not capable of establishing a linkage with an ST enterotoxin in which the disulfide bridges have been destroyed by oxidation with performic acid (Giannella R. A., Drake K. W. and Luttrel M. (1981) Infect. and Immunity 33, 186–192, so that the intramolecular disulfide bridges appear necessary for the preservation of the immunogenic properties thus shown in natural toxins.

Now Applicant company has discovered novel synthetic peptides, without intramolecular disulfide bridges, and which at the same time show remarkable relative innocousness and induce antibodies capable of establishing linkages not only with the synthetic peptidic sequence which has induced them, but quite unexpectedly and surprisingly, with pig or human natural ST enterotoxin, and by neutralising the toxicity, despite the fact that the pig or human ST enterotoxin has intramolecular disulfide bridges.

By intramolecular disulfide bridges, are denoted linkages capable of being established between the sulphur atoms of two cysteyl residues belonging to the same peptidic chain. However this expression does not exclude the possibility of the existence, in the peptides according to the invention, of a disulfide linkage between the sulphur atom of a cysteyl residue belonging to a first peptidic chain and the sulphur atom of another cysteyl residue belonging to a second peptidic chain.

It is an object of the invention to provide non-toxic synthetic peptides, stable in biological conditions and having particularly interesting properties in respect to toxic natural ST enterotoxins.

It is an object of the invention to provide non toxic synthetic peptides capable of inducing antibodies which recognise on the one hand the peptides from which they have been induced, and on the other hand, human and animal natural ST enterotoxins, particularly from pigs.

It is also an object of the invention to provide non toxic synthetic peptides which, in association with various suitable carrier molecules, are capable of inducing antibodies which neutralise the toxicity of the human and animal ST enterotoxins, particularly porcine enterotoxins.

It is also an object of the invention to provide synthetic peptides useful as stable antigenic determinants.

It is also an object of the invention to provide non toxic synthetic peptides which can be used in the application of radio-immunological tests or of immuno-enzymatic tests, agglutination tests, for example, of red blood corpuscles or of latex to detect the presence of human or animal, particularly porcine, ST enterotoxins.

It is also an object of the invention to provide non toxic synthetic peptides enabling the immunisation of man and of animal with respect to human or animal, particularly porcine, ST enteroroxins.

It is an object of the invention to provide a process enabling to obtain directly non-toxic peptides and consequently, useful without any necessary recourse to detoxification and purification steps.

It is also an object of the invention to provide a process enabling to obtain, in large amounts, synthetic peptides of predetermined structure. In one of its first aspects, the invention relates to a peptide (P)n, comprising at the most 18n amino-acids and at least 4n amino-acids, preferably levorotatory, characterized in that:

n is equal to 1 or 2 and in that when n is equal to 1, the peptidic sequence P is contained in the following peptidic chain:

Asn—Thr—Phe—Tyr—Cys—Cys—Glu—Leu—Cys—Cys—A—Pro—Ala—Cys—Ala—Gly—Cys—T  (I)

(N—ter)  (C—ter)

in which A represents Asn and T represents Tyr or A represents Tyr and T represents Asn; and characterized in that the thiol groups of the possible cysteyl residues present in the molecule have been protected by stable groups under biological conditions, one at most of the 10 thiol groups being liable to be in the form of a free SH group or to be protected by a group non-stable under biological conditions, and in that when n is equal to 2, the peptidic sequence P-P is constituted by 2 peptidic sequences P, identical or different, comprising each at most 18 amino-acids and at least 4 amino-acids, contained in the peptidic chain of formula (I) above indicated, the 2 peptidic sequences P being connected together:

through a disulfide linkage established between the sulfur atom of anyone of the cysteyl residues of one of the 2 sequences and the sulfur atom of anyone of the cysteyl residues of the other sequence;

or through a linkage established between the carboxyl group of one of the 2 peptidic sequences P and the amino group of the other sequence; and in that one at most ot the thiol groups, if it is non engaged in a disulfide linkage, can be in the form of a free SH group or protected by a non-stable group under biological conditions and the other thiol groups of the possible cysteyl residues or protected by protective groups stable under biological conditions.

In one of the preferred aspects of the invention, the peptidic sequences P are identical.

In one of its preferred aspect, the invention relates to a peptide (P)n comprising at the most 18n amino-acids and at least 4n amino-acids, characterized in that:

n is of value 1 when the P peptidic sequence does not include any cysteyl residue;

n is of value 1 or 2, when the peptidic squence P includes at least one cysteyl residue; and in that, when n is of value 1, the peptidic sequence P is contained in the following peptidic chain:

Asn—Thr—Phe—Tyr—Cys—Cys—Glu—Leu—Cys—Cys—A—Pro—Ala—Cys—Ala—Gly—Cys—T  (I)

(N—ter)  (C—ter)

in which either A represents Asn and T represents Tyr, or A represents Tyr and T represents Asn; and characterized in that the thiol groups of the possible cysteyl residues present in the molecules have been protected by one of the groups stable under the biological conditions, one at the most of the thiol groups being liable to be in the form of a free SH group or being liable to be protected by a group unstable under biological conditons; and in that when n is of value 2, the peptidic sequence P-P is constituted by two identical peptidic sequences P each including at the most 18 amino-acids and at least 4 amino-acids, contained in the peptidic chain of formula (I) as indicated above, the two peptidic sequences P being linked together through a disulfide linkage established between the sulfur atom of any one of the cysteyl residues of one of the 2 sequences and the sulfur atom of any one of the cysteyl residues of the other sequence, and characterized in that other thiol groups, possibly present, not engaged in the disulfide linkage of the possible cysteyl residues are protected by a protective group stable under biological conditions.

Generally, the invention relates to any peptide containing one or several P sequences such as they have been previously defined and capable of inducing in vivo antibodies against ST enterotoxins, these various P sequences being moreover connectable wih one another by bridging groups, themselves peptidic or not, to the extent that these bridging groups do not interfere with the immunogenic qualities attributable to the antigenic determinants which contain the P sequences concerned.

Generally, the invention relates to any peptide corresponding to the above said condition which, if necessary, after fixing to a suitable macromolecular support, is capable of inducing in vivo the production of antibodies which are active against peptides as defined above, in relationship with one of the first aspects of the invention, or more particularly against natural ST enterotoxins.

By way of example of peptidic bridges, may be mentioned oligomers of L-lysine, obtaining, for example, up to 10 lysine units, preferably 5, or again, for example, adipimate derivatives of groups linking the amine functions borne by separate P peptidic sequences.

Generally, it is possible to resort, for the constitution of all these bridging groups, to any molecule including functional groups such as amine or carboxylic, capable of reacting with respectively carboxylic and amine functions belonging to separate P sequences. Other bridging groups may precisely also bring into play entirely free SH groups of the above defined P sequences, when they contain them.

The term peptide encompasses below the peptides which are denoted by monopeptides and those which are denoted by dipeptides.

The monopeptides correspond to the case where n is equal to 1, that is to say, a peptidic chain in which each amino-acyl residue is engaged with the one or more adjacent amino-acyl residues through one or more peptidic linkages.

The dipeptides correspond to the case where n is equal to 2, that is to say, the case where the peptide includes two identical peptidic chains, in which each of the maino-acyls is engaged, with the two adjacent amino-acyls by a peptidic linkage, these two peptidic chains being connected to one another through a disulfide linkage established between the sulfur atom of any cysteyl residue of one of the chains with the sulfur atom of any cysteyl residue of the other chain.

By non stable groups under biological conditions, are designated the protective groups, the fixation of which to the thiol groups is reversible. In other words, these non stable groups remain fixed to the thiol groups only when they are present in a sufficient concentration. When the concentration is not sufficient enough, non stable groups separate from the thiol groups. The limit concentration under which non stable groups separate depends on the nature of reactions, of reaction conditions and of the compounds containing said thiol groups to be protected. By way of example of non stable groups under biological conditions, one may cite: beta-mercaptoethanol, dithiothreitol, mercury chloride, para-chloromercurobenzene, 4,4'-dithio-dipyridine.

By groups stable under biological conditions, is meant the protective groups which after having been fixed to the thiol groups, remain fixed there even when the peptides are contacted with a biological medium, despite metabolic reactions capable of intervening or any other reaction which can modify the characteristics of the peptides. These protective groups thus prevent the formation of intramolecular disulfide bridges which, if they were formed, would confer toxic properties on the peptides.

A preferred class of peptides according to the invention is constituted by those in which the amino-acids are levorotatory.

In the peptides according to the invention, any protective group of the thiol function, to the extent that it is stable under biological conditions; is suitable.

By way of example of protective groups of the thiol function and stable under biological conditons, may be cited those which are mentioned in pages 137 to 164 of the article entitled "Sulfhydryl group protection in peptide synthesis" or R. G. HISKEY, The Peptides, vol. 3 (1981), and in pages 233 to 247 of the article entitled "Solid phase peptide synthesis" by G. Barany and R. B. Merrifield, The Peptides, vol. 3 (1981).

By way of protective groups, recourse may also be had to the groups which are used in biochemistry for the final modification of thiol functions on proteins.

In practice, the protective group of the thiol function must be compatible with the conditions of synthesis used for obtaining the peptides according to the invention and in particular stable under the conditions of synthesis, including that of the final deprotection.

In fact, several interdependant parameters have to be taken into consideration in the choice of the protective group for the thiol function, since the type of synthesis itself applied determines particularly the nature of the protective groups of the acid and the amine functions to be used, which themselves determine the final deprotection agent.

In practice, recourse is had advantageously, to protect the thiol function, to the groups derived from the molecules of formula:

In this case, the protected thiol function may be represented as follows:

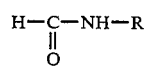

As protective groups of the thiol function, the groups derived from the compound of the following formula are advantageous:

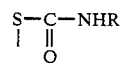

in which R, R' and R'' represent independantly of one another a hydrogen atom, an alkyl radical of 1 to 4 carbon atoms.

Among these compounds, the compounds of formula:

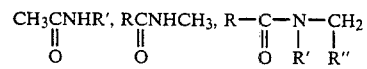

in which R and R' represent a hydrogen atom, an alkyl radical having from 1 to 4 carbon atoms are advantageous.

The thiol functions protected by each of the three above indicated protective groups may then respectively be represented by:

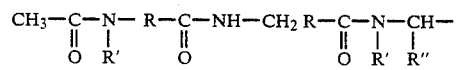

being understood that S belongs to the protected cysteyl group.

In practice, it is particularly advantageous to use acetamidomethyl or formamidomethyl. These two protective groups for the thiol function are stable under biological conditions and have the advantage of not being deprotected by the final deprotection reactions generally used and which serve on the one hand to separate the synthetic peptide from the support on which it has generally been prepared and on the other hand, to eliminate the protective groups of the acid and amine functions generally used in the course of the synthesis.

A preferred class of peptides according to the invention denoted below by G1, is constituted by the monopeptides.

These monopeptides according to the invention include at the most 18 amino-acids and at least 4 amino-acids and are characterized in that their peptide chain is contained in the following peptide sequence:

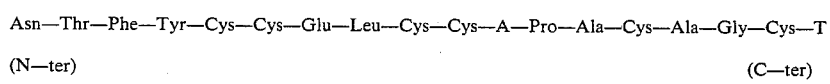

in which, either A represents Asn and T represents Tyr, or A represents Tyr and T represents Asn; and in that the thiol groups of the possible cysteyl residues present in the molecule are protected by groups stable under biological conditions, one at most of the thiol groups can be in the form of a free SH group or can be protected by a group which is unstable under biological condtions.

Among class G1, a class of preferred monopeptides according to the invention is constituted by those in which all the thiol groups of the possible cysteyl residues have been protected by groups stable under biological conditions. This class will be denoted below by G1A.

Another class of preferred monopeptides according to the invention is constituted by those in which all the thiol groups of the possible cysteyl residues, except one, have been protected by groups stable under the deprotection conditions. This class of monopeptides will be denoted below by G1B.

In the case of the peptides belonging to G1B, the only thiol group which has not been protected by a group stable under biological conditions, may be in the condition of a free SH group (or may have been protected by a group unstable under biological conditions).

When the group is unstable under the conditions of deprotection, in the course of this step, the protective group is removed and the thiol group is then to be found again in the state of a free SH group or of mixed disulfide.

By way of examples of groups protecting the SH group capable of being liberated in the course of deprotection, may be mentioned the paramethoxybenzyl group or the S-tertiobutylsulfenyl group.

In the peptidic chains indicated below, by way of example, it is understood that the end amino-acyl at the left of the sequences indicated, is an N-terminal amino-acyl and that the end amino-acyle to the right of the formula, is a C-terminal amino-acyl, except when otherwise specified. For example, Asn-Thr-Phe-Tyr corresponds to the peptidic chain in which Asn is the N-terminal group and Tyr is the C-terminal group.

Among the classes G1, G1A and G1B, a preferred class of peptides according to the invention is constituted by the peptides which comprise one of the following sequences:
 -Asn-Thr-Phe-Tyr-
 -Asn-Thr-Phe-Tyr-Cys-
 -Cys-Cys-Asn-Pro-Ala-Cys
 -Cys-Cys-Tyr-Pro-Ala-Cys-
 -Asn-Thr-Phe-Tyr-Cys-Cys-Glu-
 -Asn-Thr-Phe-Tyr-Cys-Cys-Glu-Leu-
 -Cys-Cys-Gly-Leu-Cys-Cys-Asn-Pro-Ala-Cys-Ala-Gly-Cys-
 -Cys-Cys-Gly-Leu-Cys-Cys-Tyr-Pro-Ala-Cys-Ala-Gly-Cys- Within this class defined above, a sub-class of preferred peptides according to the invention is constituted by those which correspond to the following formula:
 Asn-Thr-Phe-Tyr
 Asn-Thr-Phe-Tyr-Cys
 Cys-Cys-Asn-Pro-Ala-Cys
 Cys-Cys-Tyr-Pro-Ala-Cys
 Asn-Thr-Phe-Tyr-Cys-Cys-Glu
 Asn-Thr-Phe-Tyr-Cys-Cys-Glu-Leu
 Cys-Cys-Gly-Leu-Cys-Cys-Asn-Pro-Ala-Cys-Ala-Gly-Cys
 Cys-Cys-Gly-Leu-Cys-Cys-Tyr-Pro-Ala-Cys-Ala-Gly-Cys The three following peptides are particularly preferred:
 Asn-Thr-Phe-Tyr-Cys-Cys-Gly-Leu-Cys-Cys-Asn-Pro-Ala-Cys-Ala-Gly-Cys-Tyr (1)
 Asn-Thr-Phe-Tyr-Cys-Cys-Gly-Leu-Cys-Cys-Tyr-Pro-Ala-Cys-Ala-Gly-Cys-Asn (2)

Asn-Thr-Phe-Tyr-Cys-Gly-Gly-Gly (3)

Another class of peptides according to the invention denoted below by G2 is constituted by the above-defined dipeptides in which n equals 2.

These P-P dipeptides according to the invention include at the most $18 \times 2$ amino acids and at least $4 \times 2$ amino acids and are characterized by the fact that they are constituted by two identical peptidic sequences P each including at the most 18 amino acids and at the least 4 amino acids, contained in the peptidic chain of formula (I) indicated above, the two peptidic sequences P being connected together through a disulfide linkage established between the sulfur atom of one of the cysteyl residues of one of the two peptidic sequences and the sulfur atom of one of the cysteyl residues of the other peptidic sequence characterized in that the other thiol groups—not engaged in the disulfide linkage—of the possible cysteyl residues are protected by a protective group stable under biological conditions.

Within this class G2 of compounds defined above, a preferred sub-class of dipeptides according to the invention is constituted by those in which the disulfide linkage between the two peptidic sequences P is established between two cysteyl residues, occupying the same positions on each of the peptidic sequences P.

Within the class G2 of the dipeptides P-P according to the invention, a preferred class is constituted by those in which the peptidic sequence P comprises one of the following peptidic chains:
 -Asn-Thr-Phe-Tyr-Cys-
 -Cys-Cys-Asn-Pro-Ala-Cys-
 -Cys-Cys-Tyr-Pro-Ala-Cys-
 -Asn-Thr-Phe-Tyr-Cys-Cys-Glu-
 -Asn-Thr-Phe-Tyr-Cys-Cys-Glu-Leu-
 -Cys-Cys-Gly-Leu-Cys-Cys-Asn-Pro-Ala-Cys-Ala-Gly-Cys-
 -Cys-Cys-Gly-Leu-Cys-Cys-Tyr-Pro-Ala-Cys-Ala-Gly-Cys- Within this sub-class, an advantageous class of dipeptides P according to the invention is constituted by those in which the peptidic sequence P corresponds to the following formula:
 Asn-Thr-Phe-Tyr-Cys
 Asn-Thr-Phe-Tyr-Cys-Gly-Gly-Gly (3)
 Cys-Cys-Asn-Pro-Ala-Cys
 Cys-Cys-Tyr-Pro-Ala-Cys
 Asn-Thr-Phe-Tyr-Cys-Cys-Glu
 Asn-Thr-Phe-Tyr-Cys-Cys-Glu-Leu
 Cys-Cys-Gly-Leu-Cys-Cys-Asn-Pro-Ala-Cys-Ala-Gly-Cys
 Cys-Cys-Gly-Leu-Cys-Cys-Tyr-Pro-Ala-Cys-Ala-Gly-Cys
 Asn-Thr-Phe-Tyr-Cys-Cys-Gly-Leu-Cys-Cys-Asn-Pro-Ala-Cys- Ala-Gly-Cys-Tyr (1)
 Asn-Thr-Phe-Tyr-Cys-Cys-Gly-Leu-Cys-Cys-Tyr-Pro-Ala-Cys- Ala-Gly-Cys-Asn (2)

Particularly advantageous dipeptides according to the invention have for formula, for example according to the model:

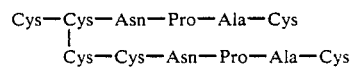

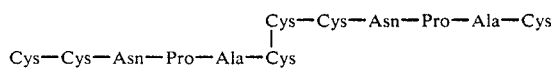

-continued

Asn—Thr—Phe—Tyr—Cys—Cys—Gly—Leu—Cys—Cys—Asn—Pro—Ala—Cys—Ala—Gly—Cys—Tyr

Asn—Thr—Phe—Tyr—Cys—Cys—Gly—Leu—Cys—Cys—Asn—Pro—Ala—Cys—Ala—Gly—Cys—Tyr

Asn—Thr—Phe—Tyr—Cys—Cys—Gly—Leu—Cys—Cys—Tyr—Pro—Ala—Cys—Ala—Gly—Cys—Asn

Asn—Thr—Phe—Tyr—Cys—Cys—Gly—Leu—Cys—Cys—Tyr—Pro—Ala—Cys—Ala—Gly—Cys—Asn

The invention relates also to conjuguates including one or several peptides according to the invention bonded covalently to a physiologically acceptable and non-toxic carrier molecule.

The carrier molecules entering into the constitution of the conjugates according to the invention are preferably selected from among biological molecules having a site of action at the level of the intestine.

By way of examples of natural proteins, may be mentioned tetanus toxin, ovalbumin, albumin serums, etc.

As synthetic macromolecular supports, may be mentioned for example polylysines or poly(D-L-alanine)-poly(L-lysine).

The literature mentions other types of macromolecular supports which can be used, which have generally a molecular weight higher than 20,000.

As a particularly advantageous carrier molecule, it is possible to resort to a carrier protein itself immunogenic insofar as the immunogenicities so conferred on the whole are not mutually troublesome.

An example of a suitable carrier protein is Shigella cytotoxin (cf. The Journal of Biological Chemistry, vol. 256, No. 16, Aug. 25, 1981, p. 8 732–8 738) or Shigella cytotoxin fragments including essential antigenic determinants of the cytotoxin of dysentery.

Another example of a particularly suitable carrier protein is choleragenoid or choleragenoid fragments comprising essential antigenic determinants of the toxin of cholera.

Choleragenoid, a non-toxic agregate of the B sub-unit of the toxin of cholera, may be purified by the method of in Infection and Immunity, June 1977, p. 789–795.

The advantage of choleragenoid is that it contains the principal antigenic determinants of the toxin of cholera and is fixed at the appropriate place, namely on the intestinal muccus in order to have effective immunity.

Consequently, the molecular conjugate constituted by choleragenoid, in association with any one of the peptides according to the invention seems particularly well suited by reason of the fact that each of the elements of the conjugate has a local immunogen activity manifested at the same place, namely at the level of the intestine.

A preferred class of conjugates according to the invention is constituted by those in which the carrier molecule is choleragenoid or Shigella cytotoxin and the peptide according to the invention comprises the following sequence:
-Asn-Thr-Phe-Tyr-
-Asn-Thr-Phe-Tyr-Cys-
-Cys-Cys-Asn-Pro-Ala-Cys-
-Cys-Cys-Tyr-Pro-Ala-Cys-
-Asn-Thr-Phe-Tyr-Cys-Cys-Glu-
-Asn-Thr-Phe-Tyr-Cys-Cys-Glu-Leu
-Cyc-Cys-Gly-Leu-Cys-Cys-Asn-Pro-Ala-Cys-Ala-Gly-Cys-
-Cys-Cys-Gly-Leu-Cys-Cys-Tyr-Pro-Ala-Cys-Ala-Gly-Cys- Another advantageous class of conjugates according to the invention is constituted by those which the carrier molecule is choleragenoid or Shigella cytotoxin and the peptide according to the invention corresponds to the following formula:
  Asn-Thr-Phe-Tyr
  Asn-Thr-Phe-Tyr-Cys
  Asn-Thr-Phe-Tyr-Cys-Gly-Gly-Cly
  Cys-Cys-Asn-Pro-Ala-Cys
  Cys-Cys-Tyr-Pro-Ala-Cys
  Asn-Thr-Phe-Tyr-Cys-Cys-Glu
  Asn-Thr-Phe-Tyr-Cys-Cys-Glu-Leu
  Cys-Cys-Gly-Leu-Cys-Cys-Asn-Pro-Ala-Cys-Ala-Gly-Cys
  Cys-Cys-Gly-Leu-Cys-Cys-Tyr-Pro-Ala-Cys-Ala-Gly-Cys
  Asn-Thr-Phe-Tyr-Cys-Cys-Gly-Leu-Cys-Cys-Asn-Pro-Ala-Cys-Ala -Cys-Tyr
  Asn-Thr-Phe-Tyr-Cys-Cys-Gly-Leu-Cys-Cys-Tyr-Pro-Ala-Cys-Ala -Cys-Asn

SYNTHESIS OF THE PEPTIDES ACCORDING TO THE INVENTION

Recourse may be had to processes known in themselves, to carry out the synthesis of the monopeptides according to the invention. These processes are summarised below.

The synthesis of the peptides in homogeneous solution and in solid phase is well known.

In this respect, recourse may be had to the method of synthesis in homogeneous solution described by HOU-BENWEYL in the treatise entitled "Methodem der Organischen Chemie" (Method of organic chemistry) edited by E. Wunsch., vol. 15-I and II, THIEME, Stuttgart 1974.

This method of synthesis consists of condensing successively in pairs the successive aminoacyls in the required order, or condensing aminoacyls and previously formed fragments and already containing several aminoacyl residues in the appropriate order, or again several fragments thus previously prepared, it being understood that care must be taken to protect previously all reactive functions borne by these aminoacyls or fragments with the exception of the amine functions of the one and the carboxyl of the other or vice versa, which must normally come into play in the formation of peptidic linkages, particularly after activation of the carboxyl function, according to well known methods in peptidic synthesis. As a modification, it is possible to resort to coupling reactions bringing into play conventional coupling reagents, of the carbodiimide type, such as, for example, 1-ethyl-3-(3-dimethyl-aminopropyl)-carbodiimide. When the aminoacyl group employed possesses an additional amine function (case of lysine, for example) or another acid function (case, for example, of glutamic acid), these functions will be, for example, protected, by carbobenzoxy or t-butyloxycarbonyl groups, as regards the amine functions, or by t-butylester groups, as regards the carboxylic functions. It is the same for the protection of any other reactive function. For example, when one of the amino acyl groups concerned contains an SH function (for example cysteine), recourse may be had to an acetamidomethyl or paramethoxybenzyl group.

In the case of progressive synthesis, amino-acid by amino-acid, the synthesis starts preferably by the condensation of the C-terminal amino-acid with the amino-acid which corresponds to the neighbouring aminoacyl in the desired sequence and so on, step by step, up to the N-terminal amino-acid. According to another preferred technique of the invention, recourse is had to that described by R. D. MERRIFIELD in the article entitled "Solid phase peptide synthesis" (J. Am . Chem. Soc., 45, 2149–2154).

To manufacture a peptidic chain according to the MERRIFIELD process, recourse is had to a very porous polymeric resin, to which the first C-terminal amino-acid of the chain is fixed. This amino-acid is fixed to the resin through its carboxyl group and its amine function is protected, for example by the t-butyloxycarbonyl group.

When the first C-terminal amino-acid is thus fixed to the resin, the protective group for the amine function is removed by washing the resin with an acid.

In the case where the protective group of the amine function is the t-butyloxycarbonyl group, it may be removed by a treatment of the resin by means of trifluoroacetic acid.

Then the second amino-acid is attached which provides the second amino-acyl of the desired sequence, from the C-terminal amino acyl residue to the deprotected amine function of the first C-terminal amino-acid fixed to the chain. Preferably, the carboxyl function of the second amino-acid is activated, for example by dicyclohexylcarbodiimid, and the amine function is protected, for example by t-butyloxycarbonyl.

In this way the first part of the desired peptidic chain is obtained, which comprises two amino-acids, and whose terminal amine function is protected. As previously, the amine function is deprotected and it is then possible to proceed with the fastening of the third aminoacyl group, under similar conditions to those of the addition of the second C-terminal amino-acid.

In this way, the amino-acids which are to constitute the peptide chain are fixed one ofter the other to the amine group each time previously deprotected of the portion of the peptide chain already formed, and which is attached to the resin.

When the whole of the desired peptide chain is formed, the protective groups of the different amino-acids constituting the peptidechain are removed and the peptide is detached from the resin, for example, by means of hydrofluoric acid.

To synthesise the dipeptides according to the invention, it is possible to resort to monopeptides.

Comprising respectively a cysteyl residue in which the thiol group is in the state of unprotected SH, particularly by oxidation in a medium containing monopeptides according to the invention, for example, by means of molecular oxygen. The medium consists, for example, of an aqueous solution of pH about 7.

This oxidation permits the disulfide linkage to establish between the sulfur atoms of the cysteyl residue including the thiol group in the state of unprotected SH.

To prepare the dipeptides according to the invention, it is also possible to resort to the indications for synthesis proposed in pages 145 to 149, of the article entitled (Sulfhydryl group protection in peptide synthesis" of R. G. Hiskey, The Peptides, Vol. 3 (1981) and in pages 240 to 243, of the article entitled "Solid phase peptide synthesis", of G. Barany and R. B. Merrifield, The Peptides, Vol. 3 (1981).

In practice, the operation is carried out as follows or in equivalent manner.

After deprotection of the peptides according to the invention, air is bubbled into the solution of the peptide until disappearance of the free thiol functions.

To synthesise the onjugates according to the invention, recourse may be had to processes know in themselves, such as that described by Frantz and Robertson in Infect. and Immunity, 33, 193–198 (1981), or that described in Applied and Environmental Microbiology, Oct. 1981, Vol. 42, No. 42, 611–614 by P. E. Kauffman by using the peptide and the appropriate carrier molecule.

In practice, the following compounds are advantageously used as coupling agents, these being mentioned in non-limiting manner: glutaric aldehyde, ethyl chloroformate, water soluble carbodiimides [N-ethyl-N' (3-dimethylamino-propyl) carbodiimide, HCl], diisocyanates, bis-diazobenzidine, di- and trichloro-s-triazines, cyanogen bromides, benzaquinone, as well as the coupling agents mentioned in Scand. J. Immunol., 1978, vol. 8, p. 7–23 (Avrameas, Ternynck, Guesdon).

It is possible to resort to any coupling process employing on one hand one or several reactive functions of the peptide and on the other hand, one or several reactive functions of the support molecules. Advantageously, carboxyl and amine functions are involved, which can give rise to a coupling reaction in the presence of a coupling agent of the type used in synthesis of proteins, for example, 1-ethyl-3-(3-dimethylamino-propyl)-carbodiimide, N-hydroxy-benzotriazole, etc. Recourse may also be had to glutaraldehyde, particularly where it is a matter of connecting to one another amine groups respectively borne by the peptide and the support molecule.

The examples which follow relate to preferred peptide synthesis according to the invention, intended to give a better illustration thereof, without however being limiting.

EXAMPLE 1

Synthesis of Monopeptide of Formula (1)

Asn—Thr—Phe—Tyr—Cys—Cys—Glu—Leu—Cys—Cys—Asn—Pro—Ala—Cys—Ala—Gly—Cys—Tyr (N—ter)          (C—ter)

This synthetic monopeptide has the same peptidic sequence as the ST enterotoxin of the pig. However with the difference from natural pig ST enterotoxin, in this monopeptide according to the invention, that all the thiol groups of the cysteyl residues are protected by acetamidomethyl and there is no intramolecular disulfide bridge. In the following, this monopeptide will be denoted by "Synthetic pig ST enterotoxin".

To prepare this monopeptide of formula (1), recourse is had to the peptide synthesis mentioned above and procedure is as follows or in equivalent manner.

The abreviations used within the scope of this synthesis have the following meaning:

BOC: t-butylcarbonyloxy
Asp: aspartic acid
Thr: threonine
Glu: glutamic acid
Pro: proline
Gly: glycine
Ala: alanine
Asn: asparagine
Cys: cysteine
Leu: leucine
Tyr: tyrosine
Phe: phenylalanine.

As amino-acids N-alpha-amino-acids protected only with the t-butyloxycarbonyl (BOC) group are used.

The side functional groups are protected as follows:
the tyrosine is protected by the 2,6-dichlorobenzyl group,
the cysteine is protected by acetamidomethyl,
the glutamic acid and the threonine are protected by benzyl.

$CH_2Cl_2$ is distilled from anhydrous $Na_2CO_3$ before use.

It is advantageous to use a resin support constituted by a 1% chloromethylated copolymer of styrene and divinylbenzene (marketed by Biorad Laboratories)

The N-alpha-t-butyloxycarbonyl-O-2,6-dichlorobenzyltyrosine is preferably esterified in the form of its cesium salt (Gisin B. F. (1973) Helv. Chim. Acta 56, 1476).

The synthesis is carried out in an automatic synthesizer of the type marketed by BECKMAN under the designation 990 B.

Each of the amino-acids entering into the constitution of the monopeptide (1) according to the invention, is fixed to the peptidic chain already formed as indicated below.

(a) The resin is washed three times for about 3 minutes with methylene chloride to suspend it.

(b) Then for about three minutes it is washed with 40% trifluoroacetic acid to impregnate the resin.

(c) It is washed again for about 30 minutes with trifluoroacetic acid to deprotect the N-terminal group of the already formed peptidic chain.

(d) It is then washed twice for about 3 minutes with methylene chloride to remove the trifluoroacetic acid.

(e) It is then washed twice for about 3 minutes with isopropyl alcohol to remove the methylene chloride.

(f) Then the medium is reimpregnated by washing four times for 3 minutes with methylene chloride.

(g) It is washed three times for about 3 minutes with diisopropylethylamine to neutralise the amine function, which becomes salified in the form of its salt with trifluoroacetic acid.

(h) It is washed four times for about 3 minutes with methylene chloride to drive off the excess of diisopropylamine.

(i) The amino-acid to be fixed to the already formed peptidic chain is added, as indicated below.

(j) It is then washed three times for about 3 minutes with methylene chloride.

(k) Then the methylene chloride is extracted by washing twice for about 3 minutes with isopropyl alcohol.

(l) It is finally washed three times for about 3 minutes with methylene chloride, to replace the reaction medium in its solvent.

As regards the fixing of each of the amino-acids to the already formed chain, recourse is had to an amino-acid (in excess with respect to the already formed peptidic chain, this excess corresponding to about three times the charge of the peptidic chain) of which the amine function is protected by the t-butyloxycarbonyl group and which the acid function is activated by dicyclohexylcarbodiimide, the hydroxybenzotriazole then added in order to minimize the side reactions. ( A. Arendt, A. M. Kolodziejzkyk (1978) Tetra-hedron Lett 40, 3867), (S. Mojsov, A. R. Mitchell (1980) J. Org. Chem. 45, 555).

After each step of adding an amino-acid, the amount of free amino-acid which is not being fixed to the peptide chain is determined by the ninhydrin test (KAISER E., COLESCOTT R. L. and al. (1976) Anal. Biochem. 34, 595), except when asparagine (at the 11 position in the peptide (1) is fixed to proline (at the 12 position in the peptide (1), the numbering being effected from left to right. When these two amino-acids are fixed, recourse is in fact had to the chloranil test (Christensen T. (1979) Acat. Chem. Scand., 833, 763). At the end of the synthesis, all the protective groups fixed to the peptide borne by the resin are eliminated, with the exception of the acetamidomethyl group which is stable with respect to this reagent (VERBER and al. (1972). J. Am. Chem. Soc. 94, 5456). The peptide of the resin is detached by means of anhydrous hydrofluoric acid in the proportion of 10 ml of anhydrous HF per gram of resin, in the presence of anisol (1 ml/g) at the temperature of about 0° C. for about 60 minutes.

After evaporation of the hydrofluoric acid, the reaction mixture is washed with ether and the peptide is separated from the resin by extraction by means of 50% acetic acid. The extracts were diluted with water and freezedried.

The crude peptide obtained is slightly water soluble. It is purified by chromatography on a column of the type marketed under the name LH 20 by using as a mobile phase the mixture dimethylformamide-acetic acid 0.1 M (3/1). Absorption at 254 nm. is measured. Various fractions of the principal peak are examined on the basis of their homogeneity and combined.

The purified peptide is obtained (97 mg, overall yield about 10%) having the following amino-acid composition:

|  | Experimental Value | Theoretical Value |
|---|---|---|
| Asp° | 2.22 | 2 |
| Thr | 0.85 | 1 |
| Glu | 1.13 | 1 |
| Pro | 1.21 | 1 |
| Gly | 1.20 | 1 |
| Ala | 2.07 | 2 |
| Cys | 4.68 | 6 |
| Leu | 1.13 | 1 |
| Tyr | 2.27 | 2 |
| Phe | 1.12 | 1 |

°The value of asparagine (Asn) is given as Asp since in the course of hydrolysis, the primary amide function of Asn is cut off, which converts it to Asp.

The purity is measured by high pressure liquid chromatography in inverse phase on a column of the type marketed under the name μ Bondapack C18 in which the eluant is the following mixture of solvents:

| $CH_3OH$ | 425 ml |
|---|---|
| $H_2O$ | 525 ml |
| Phosphate buffer | 50 ml |

-continued 0.05 M pH 2.5 with checking at 210, 254 and 270 nm.

EXAMPLE 2

Synthesis of the Monopeptide of Formula (2)

Asn—Thr—Phe—Tyr—Cys—Cys—Glu—Leu—Cys—Cys—Tyr—Pro—Ala—Cys—Ala—Gly—Cys—Asn (N—ter)                                                                             (C—ter)

The monopeptide of the above indicated sequence and in which all the thiol groups were modified by acetamidomethyl was prepared by the above indicated process.

In the following, this peptide will be denoted by "Human synthetic St enterotoxin", since it has the same amino-acid sequence as natural human ST enterotoxin. However the difference from the natural human ST enterotoxin, in the peptide according to the invention, is that all the thiol groups of the cysteyl residues are protected by acetamidomethyl, and there is no intramolecular disulfide bridge.

EXAMPLES III TO VI

They relate to the preparation of four conjugates according to the invention in which the peptide is either pig synthetic ST enterotoxin, or human synthetic ST enterotoxin, and the carrier molecule is either tetanus toxin, or ovalbumin.

In the following by ST-TT will be denoted conjugates in which the peptide according to the invention is synthetic ST enterotoxin (from pig or human) and the carrier molecule is tetanus toxin and by ST-OVA the conjugates in which the peptide according to the invention is synthetic ST enterotoxin (from pig or human) and the carrier molecule is ovalbumin.

The synthesis of these conjugates may be carried out by the method described by Frantz and Robertson in Infect. and Immunity, 33, 193–198 (1981).

The reaction mixture contains an excess of synthetic (pig or human) ST enterotoxin corresponding to about twice more synthetic ST enterotoxin than the carrier protein. Coupling between the synthetic ST enterotoxin and the various carrier proteins is effected by using, for example, 1-ethyl-3-(3-dimethyl-aminopropyl) -carbodiimide. The reaction mixture is placed to incubate in the dark for about 18 hours at ambiant temperature.

Extensive dialyse carried out on a PiNa buffer, at pH 7.00 is then resorted to, to eliminate the free synthetic ST enterotoxin and the unreacted coupling agent.

The PiNa buffer is a sodium phosphate buffer of which the composition for one litre of distilled water is as follows:

| NaCl | 8 g | NaHPO$_4$.12H$_2$O | 2.8 g |
|---|---|---|---|
| KH$_2$PO$_4$ | 0.2 g | KCl | 0.2 g |

The ST-OVA conjugates may be used directly to carry out immunisation tests on animals.

In the case of the ST-TT conjugate, it is necessary to detoxify the preparation by means of formaldehyde by the method described by BLASS et al. in Bull. Soc. Chim. 10, 3 057–3 965 (1967).

Before using the ST-TT conjugate according to the invention, its toxicity is determined by intramuscular injection in mice.

The peptides according to the invention have interesting properties with respect to human and animal natural ST enterotoxins.

The tests carried out on the peptides according to the invention are described below particularly for the following peptides:

pig synthetic ST enterotoxin according to the invention obtained as previously described;

the conjugate constituted by pig synthetic ST enterotoxin and tetanus toxin, denoted below by STP-TT;

the conjugate constituted by pig synthetic ST enterotoxin and ovalbumin, denoted below by STP-OVA.

For these tests, recourse was also had to human natural ST enterotoxin, purified as indicated below.

PURIFICATION OF HUMAN NATURAL ST ENTEROTOXIN

The ST enterotoxin to be purified is derived from a human strain of *E. coli* which only produces a enterotoxin stable to heat (strain provided by Dr. Walter Laird of NIH-USA). The conditions of growth of the bacteria and the purification of the enterotoxin are carried out according to the method described by STAPLES et al. in J. Biol. Chem. 255, 4 716–4 721.

A second pure ST enterotoxin preparation of human origin provided by Dr. R. GIANNELLA is also used in the present study.

STUDY OF THE PROPERTIES OF THE PEPTIDES ACCORDING TO THE INVENTION

1. Non toxicity

The test regarding the toxicity of the peptides according to the invention was carried out on peptides obtained by the solid phase technique described above and in which the SH groups of the cysteine residues are protected by acetamidomethyl groups.

The toxicity of the peptides according to the invention is studied by means of a test on mice described in J. Biol. Chem. 255, (1980), 4 716–4 721 by STAPLES et al. This test consists of determining the effect of the administration, to small mice, of a compound, on the accumulation of the intestinal fluid.

To do this, the compound to be tested is injected into the stomach of mice 3 or 4 days old. Then the mice are placed in an oven at 37° C. for about one hour and then anesthetised and the intestine taken out. If the intestine is swollen, then this results from the accumulation of fluid in the intestine caused by the injected compound which is hence biologically active and consequently toxic. Quantitatively, it is considered that the compound tested is biologically active, when the ratio between the weight of the intestine and the body weight is at least equal to 0.08, it being indicated that if water is injected in a control test, the ratio weight of intestine/body weight is 0.05. In the figures mentioned below, each experimental point corresponds to the average of the results obtained with three mice.

In FIG. 1, are shown the results obtained within the scope of the toxicity study of pig synthetic ST enterotoxin. As ordinates are shown the ratio weight of intestine/body weight and each column represents the average of three determinations. Column 4 corresponds to the result obtained with human natural ST enterotoxin administered in the proportion of 9 ng. Column 5 corresponds to the result obtained in the control test, without enterotoxin. The three white columns denoted by 1, 2 and 3, correspond to results obtained with synthetic ST enterotoxin administered in the proportion of 50 µg (column 1), 500 ng (column 2) and 50 ng (column 3).

From a study of this graph, it is deduced that pig synthetic ST enterotoxin is incapable of causing the accumulation of fluid in the intestinal tract of mice and consequently is not toxic.

The non toxicity of the peptides according to the invention is in accordance with the fact that they do not have intramolecular disulfide bridges, considering that the SH groups of the cysteyl residues are protected by protective groups, stable in a biological medium. Now, it has been shown that intramolecular disulfide bridges were indispensable for biological activity of pig and human natural ST toxin (STAPLES et al. in J. Biol. Chem. 255, 4 716–4 721 (1980)).

2. Immunogenic Properties

The peptides according to the invention showing in themselves to be non toxic, were tested from the immunological point of view.

The tests indicated below carried out on the conjugates according to the invention enable it to be demonstrated:

(a) that the conjugates according to the invention induce antibodies;

(b) that these antibodies react specifically with the peptides according to the invention;

(c) that these antibodies recognise natural ST enterotoxin (pig or human);

(d) that these antibodies neutralise the biological activity of natural ST enterotoxin (pig or human).

In the tests concerned below, the two following conjugates according to the invention were used:

1. Conjugate constituted by synthetic pig ST enterotoxin and ovalbumin (denoted below by STP-OVA);

2. Conjugate constituted by synthetic pig ST enterotoxin and tetanus toxin (denoted below by STP-TT); to immunise respectively rabbits and mice, by the method recognised by Frantz and Robertson described in Infect. and Immunity, 33, 193–198 (1981) by replacing the natural toxin by the two conjugates.

(a) The conjugates according to the invention induce antibodies.

(a) 1. Immunisation by means of the conjugate synthetic pig ST enterotoxin-ovalbumin The preparations of the above said conjugate according to the invention containing 100 µg of synthetic pig ST enterotoxin per ml were mixed with equal amounts of Freund adjuvants.

Intradermal injections were given to rabbits Bouscat (6 months), of 1 ml of STP-OVA conjugate at multiple places along the back.

Vaccinating doses (50 µg of synthetic pig ST enterotoxin) in suspension in incomplete Freund addulant were carried out at four week intervals over 3 months.

The rabbit serum was collected three weeks after the last injection and stored at $-20°$ C. until it was submitted to the Elisa method.

(a) 2. Immunisation by means of the conjugate synthetic pig ST enterotoxin-tetanus toxin.

Mice (Balb/c) were immunised with the conjugate STP-TT according to the following procedure. 100 µl of STP-TT conjugate (containing 10 µg of synthetic pig ST enterotoxin) were mixed with an equal volume of complete Freund adjuvants. This preparation was injected intraperitoneally.

Vaccinating injections were given in the form of intramuscular injections (100 µl of conjugate according to the invention and 100 µl of incomplete Freund adjuvant), every month, for two months. The mouse serum was collected, 4 days after the last injection. The serum was stored at $-20°$ C. until it was subjected to the Elisa method.

(a) 3. Determination of antibodies by the Elisa method (Enzyme Linked Immuno sorbent Assay).

The Elisa method is a technique in heterogeneous phase (enzyme Linked Immunosorbent Assay) which enables the determination and dosage of antibodies by means of an antigen-antibody reaction.

In general, plastic tubes are resorted to which are coated with an excess of antigens; then the serum containing the antibodies to be determined is introduced and it is left to incubate.

In the course of the incubation, the antibodies associate with their respective antigens. Then a second incubation is carried out by means of anti-immunoglobulin antibodies marked by means of an enzyme.

More precisely, the test concerning the determination of the antibodies contained in the serum of rabbit and of mouse, respectively immunised with STP-OVA and STP-TT conjugates, as indicated above, was carried out as described by Voller et al. in Enzyme linked immunosorbent Assay, a guide with abstracts of microplates applications, Dynatech, Europe, Guernsey, p. 1 (1979).

The synthetic pig ST enterotoxins or natural pig ST enterotoxins (20 µg/ml in 50 mM of carbonate/bicarbonate buffer at pH 9.0) (coating buffer) were deposited in excess on the tubes of the Elisa microplates (marketed by Nunc Inter-Med Denmark) for about two hours at about 37° C.

After deposition, the tubes were washed by means of a saline solution of sodium phosphate buffer at pH 7.4 containing 0.05% of Tween 20 (wetting agent obtained by the condensation of fatty acid esters and of sorbitol ethylene oxide, the fixing of the polyoxyethylene chains being effected on the unesterified hydroxyls of the sorbitol and marketed by the company Merck under the name Tween 20) (PiNa/Tween 20). The same buffer (PiNa/Tween 20) is also used as a diluant of rabbit and mouse serum to be tested and as a diluant of anti-immunoglobulin antibodies marked by the enzyme.

These anti-immunoglobulin antibodies are on the one hand anti rabbit goat IgGs (products by the Bionetic laboratories, USA), on the other hand sheep anti-mouse IgGs (Institut Pasteur, France), both coupled to the same enzyme, which is peroxidase.

The rabbit and mouse serums to be tested are added into the tubes in suitable dilutions and left to incubate for one hour at 37° C. After other washings with PiNa/-Tween 20, the respective anti-immunoglobulin antibodies as defined above are added and it is left to incubate for one hour at 37° C. After several washings, the amount of enzymes bonded to the tubes is determined by using O-phenylene diamine (50 mg/100 ml) and 40 µl of hydrogen peroxide in 50 mM of citrate/phosphate buffer at pH 5, as substrate. The reaction is stopped 30 minutes later, by the addition of 50 µl of 12.5% of $H_2SO_4$ and the aborption values at 492 nm are read immediately.

(b) 1. The antibodies induced by the conjugates STP-OVA and STP-TT react with synthetic pig ST enterotoxin.

In the rabbit serum to be tested, a study was made of its possibility of combining with synthetic pig ST enterotoxin.

Figure 2:
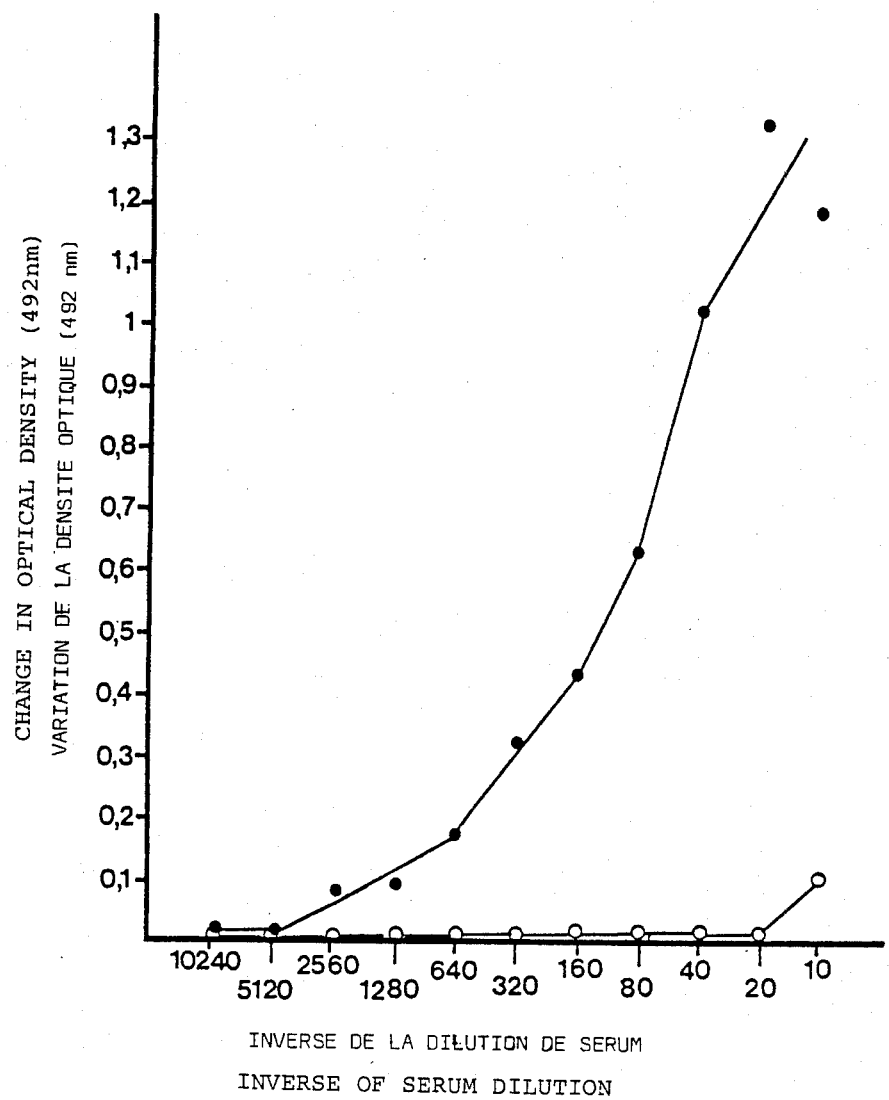

FIG. 2 represents the dosage curve (by Elisa method) of rabbit serum including antibodies enduced by the conjugate STP-OVA.

The variation of optical density as a function of the reciprocal of serum dilutions are represented as ordinates.

The curve in black dots relates to the dosage of the serum containing antibodies induced by STP-OVA conjugate.

The curve of white dots relates to serum containing antibodies induced by the STP-OVA conjugate, preincubated for one hour, at the temperature of the room with an excess of synthetic pig enterotoxin, before the Elisa method.

As it clearly results from this figure when an excess of synthetic pig ST enterotoxin is incubated with the serum before the addition to the synthetic ST enterotoxin bound to the plastic walls of the tube, no reaction is observed, which indicates that the linkage between antibodies induced by the STP-OVA conjugate and the synthetic pig ST enterotoxin is specific.

(b) 2. Antibodies induced by the conjugates STP-OVA and STP-TT react with synthetic human ST enterotoxin.

When the rabbit serum containing the antibodies induced by the conjugate STP-OVA is tested on human synthetic ST toxin, a cross reaction is observed.

FIG. 3 shows the dosage curve (by the Elisa method) of rabbit serum containing antibodies induced by the STP-OVA conjugate by synthetic human ST enterotoxin.

The optical density variation is shown as ordinates and the inverse of serum dilution as abscissae.

The curve bearing triangles corresponds to the results obtained with serum comprising antibodies induced by the STP-OVA conjugate.

The curve of white dots corresponds to the results obtained with the serum containing antibodies enduced by the STP-OVA conjugate, preincubated for about one hour, at room temperature with an excess of synthetic human ST enterotoxin, before carrying out the Elisa method.

It results clearly from this figure that antibodies induced by the STP-OVA conjugate, react with the synthetic human ST enterotoxin which is fixed to the tubes.

It is again observed therefore that the excess human synthetic ST enterotoxin, incubated with the serum to be tested, before carrying out the Elisa test, blocks the specific linkage of the antibodies induced by the STP-OVA conjugate.

(c) Antibodies induced by the STP-OVA conjugate recognizing the natural human ST enterotoxin.

In order to show that the antibodies produced against the synthetic pig ST enterotoxin are capable of reacting with the natural human ST enterotoxin, human ST enterotoxin and human synthetic ST enterotoxin were placed in cups of an Elisa microplate.

The Elisa test was carried out under these conditions, and it was observed that the above said antibodies react with natural human ST enterotoxin.

It is possible to show in the same way that the antibodies produced against synthetic pig ST enterotoxin recognize natural pig ST enterotoxin.

It is therefore deduced that the peptides according to the invention induce antibodies which recognize:
-Synthetic pig ST enterotoxin,
Synthetic human ST enterotoxin,
Natural pig ST enterotoxin,
Natural human ST enterotoxin.

(d) The peptides according to the invention induce antibodies which neutralize human natural ST enterotoxin.

The serums of rabbit and of mice which had been immunised respectively with STP-OVA and STP-TT conjugates were tested, to determine their capacity to neutralize the biological activity of natural human ST enterotoxin by resorting to the test on small mice described in J. Biol. Chem. 255 (1980), 4 716–4 721 by Staples and al.

For each test, the following six dilutions of serum in a PiNa buffer, Ph 7.00, were made:

| 1° 1/50 | 2° 1/200 | 3° 1/400 |
|---------|----------|----------|
| 4° 1/800 | 5° 1/1600 | 6° 1/3200 | and the serum to be tested was mixed with neutral human ST enterotoxin.

(d) 1. Results obtained with the antibodies induced by the STP-OVA conjugate.

In FIG. 4, is shown the effect of rabbit serum including antibodies induced by the STP-OVA conjugate on the accummulation of intestinal fluid caused by 12.5 ng of natural human ST enterotoxin (12.5 ng of ST enterotoxin representing 5 mice units, cf. Giannella R.A. (1976) Infect. and Immunity, 14, 95–99).

As ordinates are plotted the ratio weight of intestine/body weight, and as abscissae the six serum dilutions.

For each serum dilution, 12.5 ng of natural human ST enterotoxin were mixed with 20 µl of serum (Total volume 100 µl) and it was left to incubate for one hour before carrying out the test on small mice.

Each of the points on the curve obtained corresponds to the average of three determinations.

Column 1 serves as a control and corresponds to the results obtained with 12.5 ng of natural human ST enterotoxin.

Column 2 serves as a control and corresponds to the results obtained with 12.5 ng of human natural ST enterotoxin to which has been added 20 µl of unimmunised rabbit serum diluted to 1/50.

Column 3 serves as a control and corresponds to results obtained without enterotoxin.

(d) 2. Results obtained with antibodies induced by the STP-TT conjugate

Figure 5:
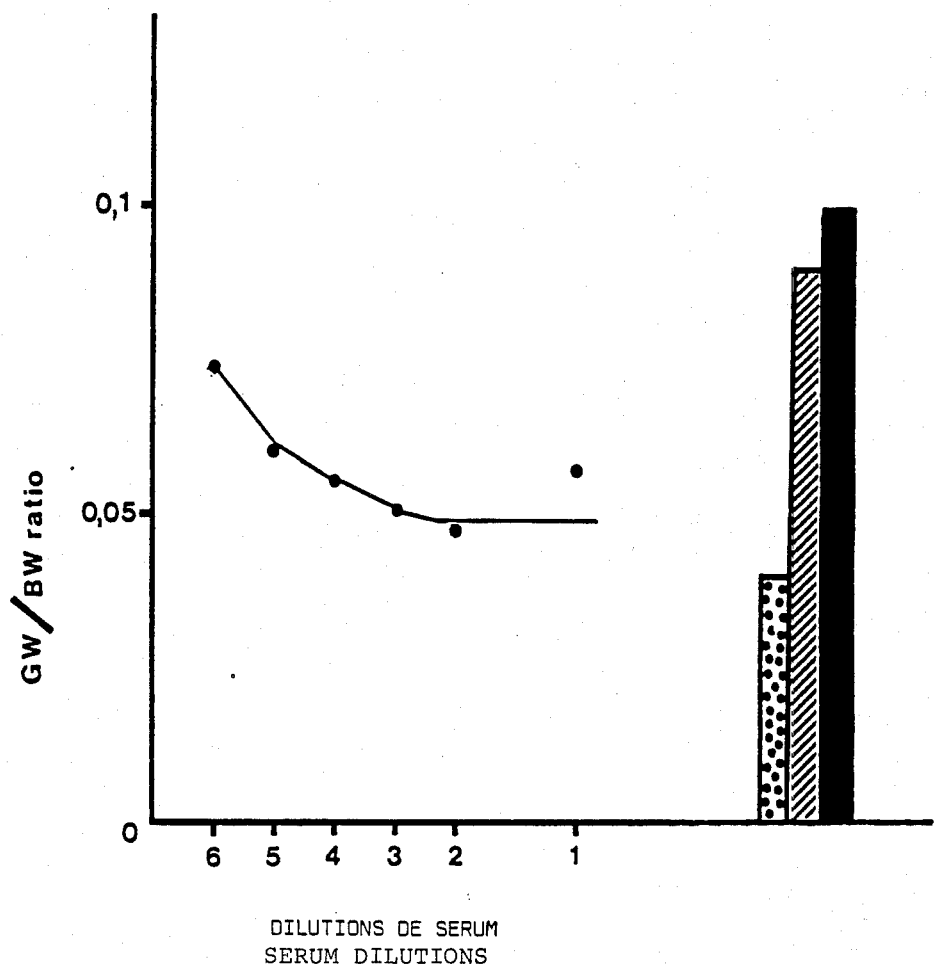

FIG. 5 shows the effect of mice serum including antibodies induced by STP-TT conjugate on the accumulation of intestinal fluid caused by 12.5 ng of natural human ST enterotoxin.

The curve of FIG. 5 is established as has been indicated with respect to FIG. 4 and the columns 1, 2 and 3 have the meanings indicated with respect to FIG. 4.

The antibodies induced by the conjugates according to the invention have the remarkable property of neutralizing specifically, the biological activity of natural human ST enterotoxin.

The peptides according to the invention which may be obtained by the process of synthesis in a solid phase have the advantage of being prepared in large amounts and in the form of homogeneous materials, which avoid resorting to complicated methods consisting of growing bacteria, followed by a compulsory purification process.

The peptides according to the invention are not toxic, even in large amount as tests have proved. This can be explained by the fact that there are no disulfide bridges, since the SH groups of the cysteyl residues are protected by groups stable in a biological medium.

The peptides according to the invention have the interesting property, when they are coupled to different carrier proteins, of inducing antibodies which recognize natural ST enterotoxin, which establish linkages with this enterotoxin and which neutralize its biological activity.

This result could be explained by the hypothesis that the four first residues Asn-Thr-Phe-Tyr of the N-terminal end of the sequence of the 18 amino-acids of the ST enterotoxin are probably not involved in the folded configuration induced by the disulfide bridges.

This portion of the ST enterotoxin appears to consist of a stable antigenic determinant, which is less immunogenic than in the folded natural ST enterotoxin, which causes antibodies when it forms part of the natural ST enterotoxin whose thiol groups of the cysteyl residues have been reduced or when it occurs in the peptide sequence of the peptides according to the invention et particularly of synthetic ST enterotoxin, whose thiol groups of the cysteyl residues are protected.

The antibodies which are directed towards this region of the molecule, bind with the natural ST enterotoxin whatever its configuration.

The example described below shows the demonstration of the ST toxin in a culture system.

EXAMPLE OF THE DEMONSTRATION OF THE ST TOXIN IN A CULTURE SYSTEM

Bacteria isolated from the sample are cultivated for 12 hours in a liquid nutrient medium, for example a yeast extract medium, casein hydrolysate (denoted by CYE).

The bacteria, after cultivation, are centrifuged and the supernatant liquor from the centrifugation is recovered.

By a conventional radio-immunological procedure the toxin contained in the supernatant liquor is determined. Thus the antibodies induced by the peptides according to the invention enable the ST toxin to be determined.

The peptides according to the invention, alone or associated with a carrier molecule are capable of inducing, as has been shown above the synthesis of neutralizing antibodies, which permit the use of the peptides as vaccinating agents.

By way of example, the peptides according to the invention (in association with a carrier molecule such as tetanus toxin) are used in the proportion of about:

10 μg for mice (Balb/c mice of about 20 g);
50 μg for rabbits of Bouscat type.

The invention is also directed to the use of the peptides for the development of radio-immunological and immuno-enzymatic tests (ELISA) to detect directly the ST enterotoxin as well as immunisation in the medical and veterinary field against natural ST enterotoxin.

The invention is naturally not limited to the particular peptides which have been envisaged.

As is well known to the technician skilled in the art, certain amino-acyl residues contained in the P sequences may if necessary be replaced by other amino-acyl residues, to the extent that the latter do not substantially modify the surface configuration of the peptides formed or the capacity of the antibodies induced by the peptides so modified with respect to unmodified peptides or in the present case, against natural ST enterotoxins. In this respect, may be mentioned for example, possible substitutions of the alanyl group by the glycyl group or vice versa, the possible substitution of the iso-asparagic residues by aspartic, glutamine or isoglutamine residues, the substitution of the valine groups by alanine, leucine or glycine groups, substitution of the lysine groups by norleucine groups or again arginine, etc., provided that there is verification each time of the capacity of the modified peptides of inducing antibodies capable of neutralizing the peptides as defined above, or the natural toxin. It is naturally understood that all these possible equivalents are covered by the peptides more specifically claimed below.

We claim:

1. A peptide (P) n free of intramolecular disulfide bridges and free of intramolecular disulfied bridges and capable of inducing in vivo antibodies against ST enterotoxins comprising 4n to 18n amino-acids, wherein - n is equal to 1 or 2, and when n is equal to 1, the peptidic sequence P is contained in the following peptidic chain:

Asn—Thr—Phe—Tyr—Cys—Cys—Glu—Leu—Cys—
           —Cys—A—Pro—Ala—Cys—Ala—Gly—
(C—ter)
Cys—T(I)
(N—ter)

in which A and T each represent Tyr or Asn; and A and T are not the same wherein all except one the thiol groups of the cysteyl residues present in the molecule are protected by a group which is stable under biological conditions, said one of said thiol groups being in the form of a free SH group or protected by a group which is unstable under biological conditions; and, when n is equal to 2, the peptidic sequence P-P is constituted by 2 peptidic sequences P, which are identical or different, each sequence comprising 4 to 18 amino-acids, contained in the peptidic chain of formula (I), the 2 peptidic sequences P being connected together through a disulfide linkage established between the sulfur atom of the cysteyl residues of one of the 2 sequences and the sulfur atom of the cysteyl residues of the other sequence;

or through a linkage established between the carboxyl group of the 2 peptidic sequences P and the amino group of the other sequences; and wherein one of the thiol groups not engaged in a disulfide linkage, being in the form of a free SH group or protected by a group that is unstable under biological conditions and the other thiol group of the possible cysteyl residues being protected by protective groups which are stable under biological conditions.

2. The peptide (P) n according to claim 1, wherein the amino-acids are levorotatory.

3. The peptide (P) n free of intramolecular disulfide bridges and capable of inducing in vivo antibodies against ST enterotoxins comprising 4n to 18n amino-acids, wherein
- n is equal to 1 when the peptidic sequence P does not include any cysteyl residue;
- n is equal to 1 or 2, when the peptidic sequence P comprises at least one cysteyl residue; and when n equals 1, the peptidic sequence P is contained in the following peptidic chain:

Asn—Thr—Phe—Tyr—Cys—Cys—Glu—Leu—Cys—Cys—A—Pro—Ala—Cys—Ala—Gly—Cys—T(I)

(N—ter) (C—ter)

in which A and T each represent Tyr or Asn and A and T are not the same; and wherein all except one of the thiol groups of the possible cysteyl residues present in the molecule are protected by groups stable under biological conditions, said one of said thiol groups being in the form of a free SH group or protected by a group which is unstable under biological conditions; and when n equals 2, the peptidic sequence P-P is constituted by two identical sequences P, each including 4 to 18 amino-acids, contained in the peptidic chain formula (I), the two peptidic sequences P being connected together through a disulfide linkage established between the sulfur atom of any one the cysteyl residue of one of the two sequences and the sulfur atom of any one of the cysteyl residues of the other sequence, and wherein the other thiol group not engaged in the disulfide linkage of the possible cysteyl residues are protected by a protective group which is stable under biological conditions.

4. The peptide according to claim 3, wherein the amino-acids are levorotatory.

5. The peptide according to claim 1, wherein the protective groups stable under biological conditions of the thiol function of the cysteyl residues are derived from a compound of the formula:

$$\overset{\text{RCNR'R''}}{\underset{\text{O}}{\|}}$$

in which R, R' and R" each represent independently of one another a hydrogen atom, an alkyl radical of 1 to 4 carbon atoms.

6. The peptide according to claim 1, characterized in that the group protecting the thiol function is an acetamidomethyl or formamidomenthyl group.

7. The peptide according to claim 1, wherein the peptidic chain is contained in the following peptidic sequence:

Asn—Thr—Phe—Tyr—Cys—Cys—Glu—Leu—Cys—Cys—A—Pro—Ala—Cys—Ala—Gly—Cys—T(I)

(N—ter) (C—ter)

in which either A and T represent Tyr or Asn in which A and T are different; wherein the thiol groups of the cysteyl residues present in the molecule are protected by groups stable under biological conditions, one of and thiol groups being in the form of a free SH group or protected by a group unstable under biological conditions.

8. The peptide according to claim 1, wherein the peptidic chain is contained in the following peptidic sequence:

Asn—Thr—Phe—Tyr—Cys—Cys—Glu—Leu—Cys—Cys—A—Pro—Ala—Cys—Ala—Gly—Cys—T (N—ter) (C—ter)

wherein A and T each represent Tyr or Asn and A and T are different; and wherein the thiol groups of the cysteyl residues present in the molecule are protected by residues derived from a compound of the formula:

$$\overset{\text{RCNR'R''}}{\underset{\text{O}}{\|}}$$

in which R, R' and R" represent independently of one another a hydrogen atom or an alkyl radical of 1 to 4 carbon atoms, one of the thiol groups being in the form of a free SH group or protected by a group which is unstable under biological conditions.

9. The peptide according to claim 1, wherein the peptidic chain is contained in the following peptidic sequence:

Asn—Thr—Phe—Tyr—Cys—Cys—Glu—Leu—Cys—Cys—A—Pro—Ala—Cys—Ala—Gly—Cys—T (N—ter) (C—ter)

wherein A and T each represent Tyr or Asn and A and T are not the same; and wherein the thiol groups of the possible cysteyl residues present in the molecule are protected by an acetamidomethyl or formamidomethyl, group; one of the thiol groups being in the form of a free SH group or protected by a group which is unstable under biological conditions.

10. The peptide according to claim 1, wherein the peptidic chain is contained in the following peptidic sequence:

Asn—Thr—Phe—Tyr—Cys—Cys—Glu—Leu—Cys—Cys—A—Pro—Ala—Cys—Ala—Gly—Cys—T (N—ter) (C—ter)

in which either A amd T each represent Tyr or Asn, and A and T are not the same; and wherein all the thiol groups of the cysteyl residues are protected by groups stable under biological conditions.

11. The peptide according to claim 1, wherein the peptidic chain is contained in the following peptidic sequence:

Asn—Thr—Phe—Tyr—Cys—Cys—Glu—Leu—Cys—Cys—A—Pro—Ala—Cys—Ala—Gly—Cys—T (N—ter) (C—ter)

in which either A and T each represent Tyr or Asn, and A and T are not the same; and wherein all the thiol groups of the cysteyl residues are protected by groups derived from a compound of the formula:

in which R, R' and R" represent independently of one another a hydrogen atom, an alkyl radical of 1 to 4 carbon atoms.

12. The peptide according to claim 1, wherein the peptidic chain is contained in the following peptidic sequence:

Asn—Thr—Phe—Tyr—Cys—Cys—Glu—Leu—Cys—Cys—A—Pro—Ala—Cys—Ala—Gly—Cys—T (N—ter) (C—ter)

A and T each represent Tyr or Asn, and A are different and wherein the thiol groups of the cysteyl residues are protected by an acetamidomethyl or formamidomethyl group.

13. The peptide according to claim 1, wherein the peptidic chain is contained in the following peptidic sequence:

Asn—Thr—Phe—Tyr—Cys—Cys—Glu—Leu—Cys—Cys—A—Pro—Ala—Cys—Ala—Gly—Cys—T (N—ter) (C—ter)

in which either A and T each represent Tyr or Asn, and A and T are different; and wherein the thiol groups of the cysteyl residues, except one, are protected by groups stable under biological conditions.

14. The peptide according to claim 1, wherein the peptidic chain is contained in the following peptidic sequence:

Asn—Thr—Phe—Tyr—Cys—Cys—Glu—Leu—Cys—Cys—A—Pro—Ala—Cys—Ala—Gly—Cys—T (N—ter) (C—ter)

in which either A and T each represent Tyr or Asn, and A and t are different; and wherein all except one of the thiol groups of the cysteyl residues are protected by groups derived from a compound of the formula:

in which R, R' and R" represent independently of one another a hydrogen atom or an alkyl radical of 1 to 4 carbon atoms.

15. The peptide according to claim 1, wherein the peptidic chain is contained in the following peptidic sequence:

Asn—Thr—Phe—Tyr—Cys—Cys—Glu—Leu—Cys—Cys—A—Pro—Ala—Cys—Ala—Gly—Cys—T (N—ter) (C—ter)

in which either A and T each represent Tyr or Asn, and A and T are different; and wherein all except one of the thiol groups of the possible cysteyl residues, are protected by an acetamidomethyl or formamidomethyl group.

16. The peptide according to claim 1, having two identical peptidic sequences P and each including 4 to 18 amino acid groups contained in the peptidic chain of formula (I), the two peptidic sequences P being connected together through a disulfide linkage established between the sulfur atom of one of the cysteyl residues and one of the two peptidic sequences and the sulfur atom of one of the cysteyl residues of the other peptidic sequence, and wherein other thiol groups not engaged in the disulfide linkage of cysteyl residues are protected by protective groups stable under biological conditions.

17. The peptide according to claim 1, having two identical peptidic sequences P each including 4 to 18 amino acid groups contained in the peptidic chain of formula (I), the two peptidic sequences P being connected together through a disulfide linkage established between the sulfur atom of one of the cysteyl residues and one of the two peptidic sequences and the sulfur atom of one of the cysteyl residues of the other peptidic sequence, and wherein the thiol groups not engaged in the disulfide linkage of the cysteyl residues are protected by groups derived from a compound of the formula:

in which R, R' and R" represent independently of one another a hydrogen atom, or an alkyl radical of 1 to 4 carbon atoms.

18. The peptide according to claim 1, having two identical peptidic sequence P each including 4 to 18 amino acid groups contained in the peptidic chain of formula (I), the two peptidic sequences P being connected together through a disulfide linkage established between the sulfur atom of one of the cysteyl residues and one of the two peptidic sequences and the sulfur atom of one of the cysteyl residues of the other peptidic sequence, and wherein the thiol groups not engaged in the disulfide linkage of the cysteyl residues are protected by an acetamidomethyl or formamidomethyl group.

19. The peptides according to claim 1, comprising one of the following sequences:
 -Asn-Thr-Phe-Tyr-
 Asn-Thr-Phe-Tyr-Cys-
 -Cys-Cys-Asn-Pro-Ala-Cys-
 -Cys-Cys-Tyr-Pro-Ala-Cys-
 -Asn-Thr-Phe-Tyr-Cys-Cys-Glu-
 -Asn-Thr-Phe-Tyr-Cys-Cys-Glu-Leu-
 -Cys-Cys-Gly-Leu-Cys-Cys-Asn-Pro-Ala-Cys-Ala-Gly-Cys-
 Cys-Cys-Gly-Leu-Cys-Cys-Tyr-Pro-Ala-Cys-Ala-Gly-Cys.

20. The peptides according to claim 1, having one of the following sequences:
 -Asn-Thr-Phe-Tyr-
 -Asn-Thr-Phe-Tyr-Cys-
 -Cys-Cys-Asn-Pro-Ala-Cys-
 -Cys-Cys-Tyr-Pro-Ala-Cys-
 -Asn-Thr-Phe-Tyr-Cys-Cys-Glu-
 -Ans-Thr-Phe-Tyr-Cys-Cys-Glu-Leu-
 -Cys-Cys-Gly-Leu-Cys-Cys-Asn-Pro-Ala-Cys-Ala-Gly-Cys-
 -Cys-Cys-Gly-Leu-Cys-Cys-Tyr-Pro-Ala-Gly-Cys-
 Asn-Thr-Phe-Tyr-Cys-Cys-Gly-Leu-Cys-Cys-Asn-Pro-Ala-Cys-
 Ala-Gly-Cys-Tyr (1)
Asn-Thr-Phe-Tyr-Cys-Cys-Gly-Leu-Cys-Cys-Tyr-Pro-Ala-Cys- Ala-Gly-Cys-Asn (2)
 Asn-Thr-Phe-Tyr-Cys-Gly-Gly-Gly (3)

21. A conjugate comprising a peptide according to claim 1 in association with a physiologically acceptable and non-toxic carrier molecule.

22. A composition for producing antibodies enabling the demonstration of human or animal ST toxins, particularly of pigs which comprises cultivating a peptide according to claim 1 and a non-toxic carrier molecule.

23. A pharmaceutical composition for producing antibodies enabling the vaccination of man or animals with respect to human or animal ST enterotoxins particularly of pigs which comprises a peptide according to claim 1 and a non-toxic carrier molecule.

24. The peptide according to the claim 5 wherein the protective group of the thiol function of the cysteyl residue has the formula

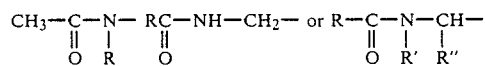

in which R, R' and R" are as hereinbefore described.

25. The peptide according to claim 8 wherein the protective group of the thiol function of the cysteyl residue has the formula

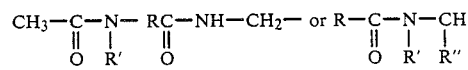

wherein R, R' and R" are as hereinbefore described.

26. The peptide according to claim 11 wherein the protective group of the thiol function of the cysteyl residue has the formula

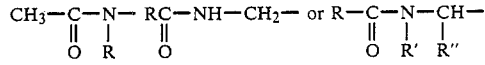

wherein R, R' and R" are as hereinbefore described.

27. The peptide according to claim 14 wherein the protective group of the function of the cysteyl residue has the formula

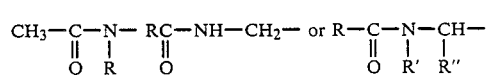

wherein R, R' and R" are as hereinbefore described.

28. The peptide according to claim 17 wherein the protective group of the function of the cysteyl residue has the formula

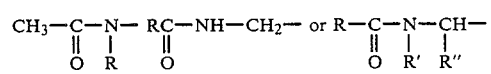

wherein R, R' and R" are as hereinbefore described.

29. The conjugate according to claim 21 wherein said non-toxic carrier molecule is a protein.

30. The conjugate according to claim 29 wherein the protein is selected from the group consisting of ovalbumin, tetanus toxin, choleragenoid and shigella cytotoxin.

31. A conjugate of a carrier molecule which is choleragenoid or Shigella cytotoxin and a peptide selected from the group consisting of:
 Asn-Thr-Phe-Tyr,
 Asn-Thr-Phe-Tyr-Cys,
 Asn-Thr-Phe-Tyr-Cys-Gly-Gly-Gly,
 Cys-Cys-Asn-Pro-Ala-Cys,
 Cys-Cys-Tyr-Pro-Ala-Cys,
 Asn-Thr-Phe-Tyr-Cys-Cys-Glu,
 Asn-Thr-Phe-Thy-Cys-Cys-Glu-Leu,
 Cys-Cys-Gly-Leu-Cys-Cys-Asn-Pro-Ala-Cys-Ala-Gly-Cys,
 Cys-Cys-Gly-Leu-Cys-Cys-Tyr-Pro-Ala-Cys-Ala-Cly-Cys,
 Asn-Thr-Phe-Tyr-Cys-Cys-Gly-Leu-Cys-Cys-Asn-Pro-Ala-Cys-Ala
 -Cys-Tyr,
 Asn-Thr-Phe-Tyr-Cys-Cys-Gly-Leu=Cys-Cys-Tyr-Pro-Ala-Cys-Ala
 -Cys-Asn,

```
           Cys—Cys—Asn—Pro—Ala—Cys
               |
           Cys—Cys—Asn—Pro—Ala—Cys,

Cys—Cys—Asn—Pro—Ala—Cys
                               |
Cys—Cys—Asn—Pro—Ala—Cys

Asn—Thr—Phe—Tyr—Cys—Cys—Gly—Leu—Cys—Cys—Asn—Pro—Ala—Cys—Ala—Gly—Cys—Tyr
                                                                 |
Asn—Thr—Phe—Tyr—Cys—Cys—Gly—Leu—Cys—Cys—Asn—Pro—Ala—Cys—Ala—Gly—Cys—Tyr and Asn—Thr—Phe—Tyr—Cys—Cys—Gly—Leu—Cys—Cys—Tyr—Pro—Ala—Cys—Ala—Gly—Cys—Asn
                                                                 |
Asn—Thr—Phe—Tyr—Cys—Cys—Gly—Leu—Cys—Cys—Tyr—Pro—Ala—Cys—Ala—Gly—Cys—Asn
```

32. A peptide selected from the group consisting of:
Asn-Thr-Phe-Tyr,
Asn-Thr-Phe-Tyr-Cys,
Asn-Thr-Phe-Tyr-Cys-Gly-Gly-Gly,
Cys-Cys-Asn-Pro-Ala-Cys,
Cys-Cys-Try-Pro-Ala-Cys,
Asn-Thr-Phe-Tyr-Cys-Cys-Glu,
Asn-Thr-Phe-Tyr-Cys-Cys-Glu-Leu,
Cys-Cys-Gly-Leu-Cys-Cys-Asn-Pro-Ala-Cys-Ala-Gly-Cys,
Cys-Cys-Gly-Leu-Cys-Cys-Tyr-Pro-Ala-Cys-Ala-Gly-Cys,
Asn-Thr-Phe-Tyr-Cys-Cys-Gly-Leu-Cys-Cys-Asn-Pro-Ala-Cys-Ala -Cys-Tyr,
Asn-Thr-Phe-Tyr-Cys-Cys-Gly-Leu-Cys-Cys-Tyr-Pro-Ala-Cys-Ala -Cys-Asn,

```
           Cys—Cys—Asn—Pro—Ala—Cys
               |
           Cys—Cys—Asn—Pro—Ala—Cys,

Cys—Cys—Asn—Pro—Ala—Cys
                               |
Cys—Cys—Asn—Pro—Ala—Cys

Asn—Thr—Phe—Tyr—Cys—Cys—Gly—Leu—Cys—Cys—Asn—Pro—Ala—Cys—Ala—Gly—Cys—Tyr
                                                                 |
Asn—Thr—Phe—Tyr—Cys—Cys—Gly—Leu—Cys—Cys—Asn—Pro—Ala—Cys—Ala—Gly—Cys—Tyr, and Asn—Thr—Phe—Tyr—Cys—Cys—Gly—Leu—Cys—Cys—Tyr—Pro—Ala—Cys—Ala—Gly—Cys—Asn
                                                                 |
Asn—Thr—Phe—Tyr—Cys—Cys—Gly—Leu—Cys—Cys—Tyr—Pro—Ala—Cys—Ala—Gly—Cys—Asn,
```

33. A pharmaceutical compositon for inducing antibodies which neutralize the toxicity of human and animal ST enterotoxins which comprises a peptide of claim 1 and non-toxic carrier molecule.

34. A method for inducing antibodies which neutralize the toxicity against ST enterotoxins in humans or animals which comprise administering an effective amount of the composition of claim 33.

* * * * *